(12) United States Patent
Piontkowski

(10) Patent No.: US 7,253,949 B2
(45) Date of Patent: Aug. 7, 2007

(54) STEREO MICROSCOPE

(76) Inventor: Paul K. Piontkowski, 2310 Popkins La., Alexandria, VA (US) 22306

( * ) Notice: Subject to any disclaimer, the term of this patent is extended or adjusted under 35 U.S.C. 154(b) by 330 days.

(21) Appl. No.: 10/646,929

(22) Filed: Aug. 25, 2003

(65) Prior Publication Data

US 2004/0114221 A1 Jun. 17, 2004

Related U.S. Application Data

(63) Continuation-in-part of application No. 10/320,385, filed on Dec. 17, 2002.

(51) Int. Cl.
*G02B 21/00* (2006.01)
*G02B 21/06* (2006.01)

(52) U.S. Cl. .................. 359/380; 359/368; 359/385

(58) Field of Classification Search ........ 359/368–390; 351/200–244
See application file for complete search history.

(56) References Cited

U.S. PATENT DOCUMENTS

| | | | |
|---|---|---|---|
| 941,591 A | 11/1909 | Sweet | 248/282 |
| 2,479,720 A | 8/1949 | Brandt | 248/123.2 |
| 2,791,937 A * | 5/1957 | Leitz et al. | 359/376 |
| 3,090,045 A | 5/1963 | Hurst | 2/7 |
| 3,290,985 A | 12/1966 | Bains et al. | 359/896 |
| 3,434,772 A * | 3/1969 | Fogle | 359/377 |
| 3,796,220 A | 3/1974 | Bredemeier | 606/18 |
| 3,830,230 A | 8/1974 | Chester | 600/249 |
| 3,909,106 A * | 9/1975 | Buhler | 359/377 |
| 4,157,859 A * | 6/1979 | Terry | 359/375 |
| 4,175,826 A * | 11/1979 | Blaha et al. | 359/377 |
| 4,195,903 A * | 4/1980 | Kawase et al. | 359/376 |
| 4,275,949 A * | 6/1981 | Jones | 359/209 |
| 4,277,130 A * | 7/1981 | Takahashi | 359/376 |
| 4,344,595 A | 8/1982 | Heller et al. | 248/542 |
| 4,364,629 A | 12/1982 | Lang et al. | 359/377 |
| 4,396,260 A * | 8/1983 | Takizawa et al. | 351/206 |
| 4,411,627 A | 10/1983 | Breglia et al. | 434/66 |
| 4,515,333 A | 5/1985 | Pugh et al. | 248/123.11 |
| 4,518,231 A | 5/1985 | Muchel et al. | 359/376 |
| 4,592,096 A | 6/1986 | Glasheen | 2/427 |
| 4,594,608 A | 6/1986 | Hatae et al. | 348/79 |
| 4,614,411 A | 9/1986 | Hörenz | 359/375 |
| 4,616,257 A | 10/1986 | Kloots et al. | 348/370 |
| 4,657,356 A | 4/1987 | Matsumura | 359/377 |
| 4,787,734 A | 11/1988 | Matsumura | 351/212 |
| 4,849,778 A | 7/1989 | Samuelson | 396/428 |
| 5,121,220 A * | 6/1992 | Nakamoto | 359/419 |
| 5,252,070 A | 10/1993 | Jarrett | 434/59 |

(Continued)

FOREIGN PATENT DOCUMENTS

GB 2053502 2/1981

*Primary Examiner*—Thong Q Nguyen

(57) ABSTRACT

A stereo microscope includes two oculars mounted at one end of a housing and an objective lens mounted at an opposite end of the housing. Between the opposite ends of the housing is a rotatably mounted lens magnification changer with three series of bores extending diametrically therethrough. For each ocular, a line of sight extends to a prism assembly, through one of the bores of a series which contains a lens assembly and through the objective lens. Both lines of sight lie in a common plane. A LED light source is located adjacent the objective lens. Light entering through the objective lens and one of the series of bores in the lens magnification changer is received by a digital camera.

29 Claims, 4 Drawing Sheets

U.S. PATENT DOCUMENTS

| | | | |
|---|---|---|---|
| 5,253,832 A | 10/1993 | Bolas et al. | 248/123.11 |
| 5,287,219 A * | 2/1994 | Hildebrand et al. | 359/368 |
| 5,365,607 A | 11/1994 | Benevento, Jr. et al. | 2/181.4 |
| 5,420,716 A * | 5/1995 | Fukaya | 359/368 |
| 5,442,489 A * | 8/1995 | Yamamoto et al. | 359/810 |
| 5,537,248 A | 7/1996 | Sander | 359/376 |
| 5,841,509 A * | 11/1998 | Harooni et al. | 351/221 |
| 5,847,868 A * | 12/1998 | Palmer | 359/407 |
| 5,913,412 A | 6/1999 | Huber et al. | 2/414 |
| 6,081,372 A | 6/2000 | Mura | 359/377 |
| 6,147,800 A | 11/2000 | Faber | 359/389 |
| 6,290,368 B1 | 9/2001 | Lehrer | 362/187 |
| 6,606,192 B2 | 8/2003 | Haran | 359/409 |

* cited by examiner

STEREO MICROSCOPE

CROSS-REFERENCE TO RELATED APPLICATIONS

This application is a continuation-in-part of application Ser. No. 10/320,385 filed Dec. 17, 2002 to a HEAD MANIPULABLE BINOCULAR MICROSCOPE SUPPORT.

STATEMENT REGARDING FEDERALLY SPONSORED RESEARCH OR DEVELOPMENT

"Not Applicable"

BACKGROUND OF THE INVENTION

There is a need for a low cost, light weight stereo microscope having a set of oculars wherein a clinician looking into the oculars views comfortably and naturally an object to be magnified or observed. It is desirable that the two lines of sight from the clinician's eyes through the oculars and the microscope to the object to be magnified or observed lie in a common plane. This forms a comfortable situation for the clinician since when the eyes of the clinician are removed from the oculars, the clinician is looking directly at the object to be observed. Also, there is a need in a stereo microscope for an inexpensive light source and camera.

BRIEF SUMMARY OF THE INVENTION

The invention pertains to a stereo microscope wherein both lines of sight from the eyes of a clinician pass through a housing to an object to be observed or magnified and lie in a common plane. The microscope also has an LED light source and a digital camera within its housing.

DETAILED DESCRIPTION OF THE DRAWINGS

Figure 1:
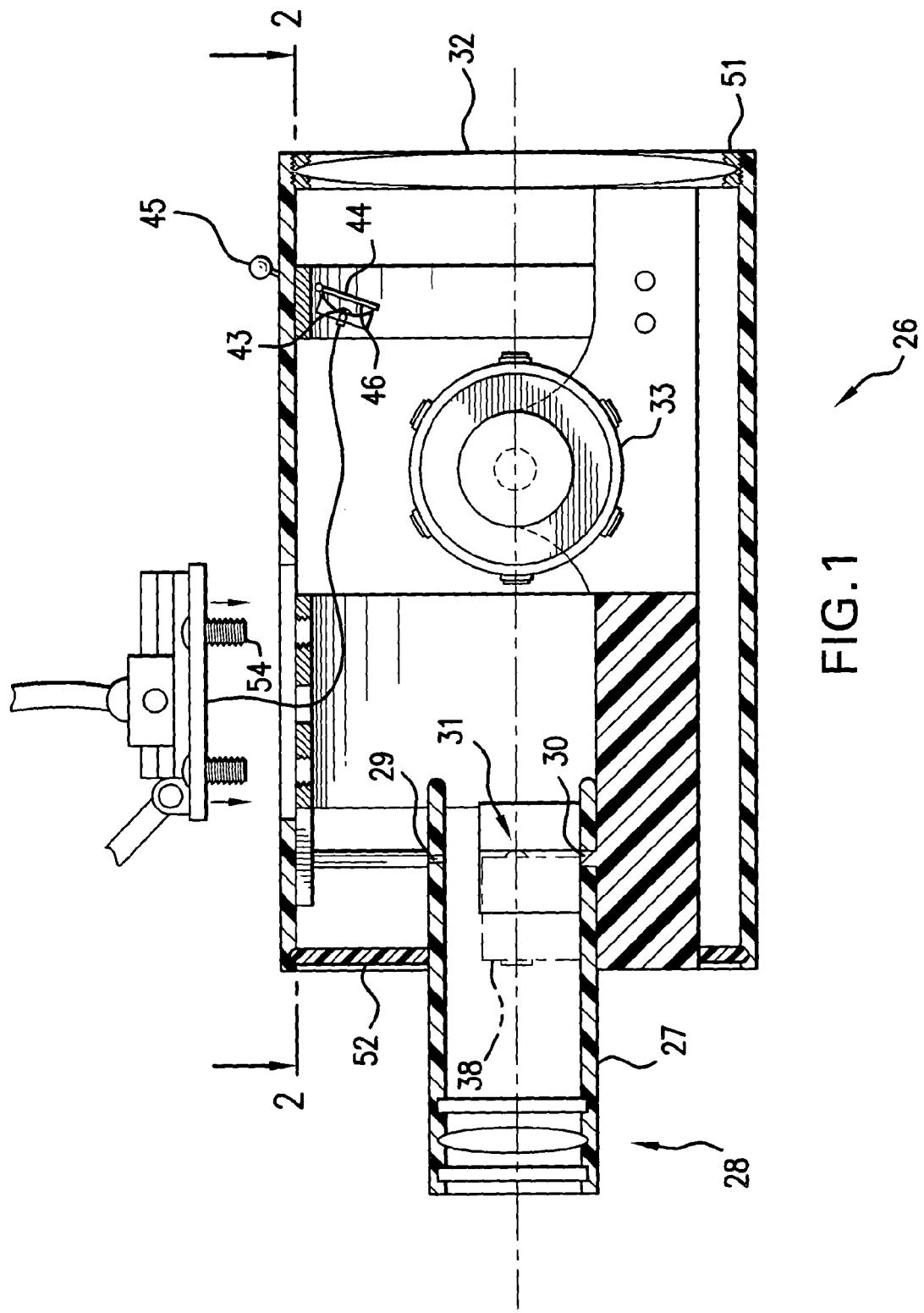
FIG. 1 shows a side elevation of the stereo microscope as taken along the section lines 1-1 in FIG.2.

The stereo microscope of this invention includes a housing or hollow elongated body 26 having a pair of oculars 27. Each ocular has a lens assembly 28 and is pivotally mounted at 29 and 30 so that both oculars move in a common plane. Adjacent an end of each ocular is a prism assembly 31. An objective lens 32 is mounted in the housing at an end opposite the pair of oculars. Located between the prism assemblies 31 and the objective lens 32 is a lens magnification changer 33. The lens magnification changer is rotatively mounted at 34. A first series of bores 35 extend diametrically through the lens magnification changer 33 and with all bores located in a common plane. Two or more of these bores contain a lens assembly. A second series of bores 36 extend diametrically through the lens magnification chamber 33 and all located in a common plane. Two or more of these second series of bores contain a lens assembly. A line of sight is established through each ocular 27 to a prism assembly 31, through one of the bores of the lens magnification changer and through the objective lens 32. The lines of sight extending through each ocular 27 and the remainder of the stereo microscope both lie in a common plane. This provides the advantage over conventional stereo microscopes of shortening the optical paths through the microscope which improves light transmission and provides less distortion of an image observed. Pivotally mounting each of the oculars provides for adjusting an angle between each optical path extending through an ocular and an optical path extending through a respective bore of the lens magnification changer to improve the stereoscopic image of an object observed. Increasing the amount of spacing between the bores 35 and 36 of the lens magnification changer 33 improves the stereoscopic effect of the image observed.

A digital camera 38 may be used with the stereo microscope. The camera is positioned adjacent an end of the housing. The lens magnification changer includes a third series of bores 37 located axially between the first 35 and second 36 series of bores, about the periphery of the lens magnification changer in a common plane, and extending diametrically through the lens magnification changer. This third series of bores 37 may all contain a lens assembly, or one or more may not contain a lens assembly. Light passes through the objective lens 32, one of the bores 37 of the lens magnification changer, and to the camera 38. There is a spring biased rod 39 that mates with one of a plurality of indents in an axis of the lens magnification changer to align bores of the lens magnification changer with the line of sight and the camera. A knob 40 is used for rotating the lens magnification changer.

Figure 2:
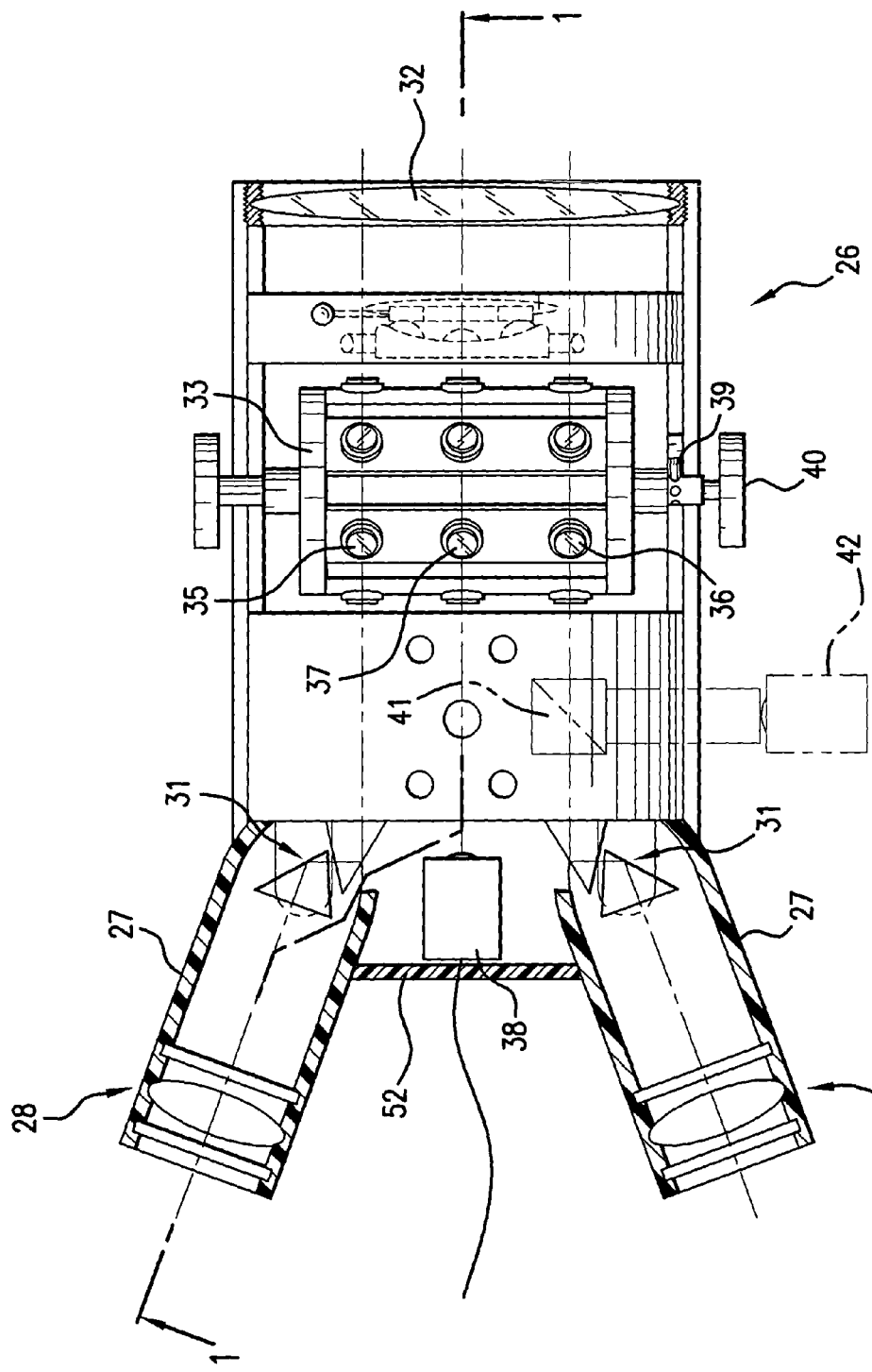
FIG. 2 is a plan view of the stereo microscope as taken along the section lines 2-2 in FIG. 1.

In FIG. 2, an alternate modification of the camera is disclosed in dashed lines. A beam splitter 41 may be located in a line of sight for an ocular. Part of the light would pass through to the ocular and part of the light would be reflected to a camera 42 located at a side of the stereo microscope.

Located at one end of the housing 26 and adjacent the objective lens 32 is a light emitting diode (LED) light source 43 which may be either one or a plurality of LED's. However, other light sources may be used. A suitable reflector 46 is positioned in back of the light source 43 and a light filter 44 is located in front of the light source. The light filter is hinged at its upper part and attached to a lever 45 which is located outside the housing 26. By controlling the lever 45, the filter can be positioned either in front of the light source or out of the way.

Figure 3:
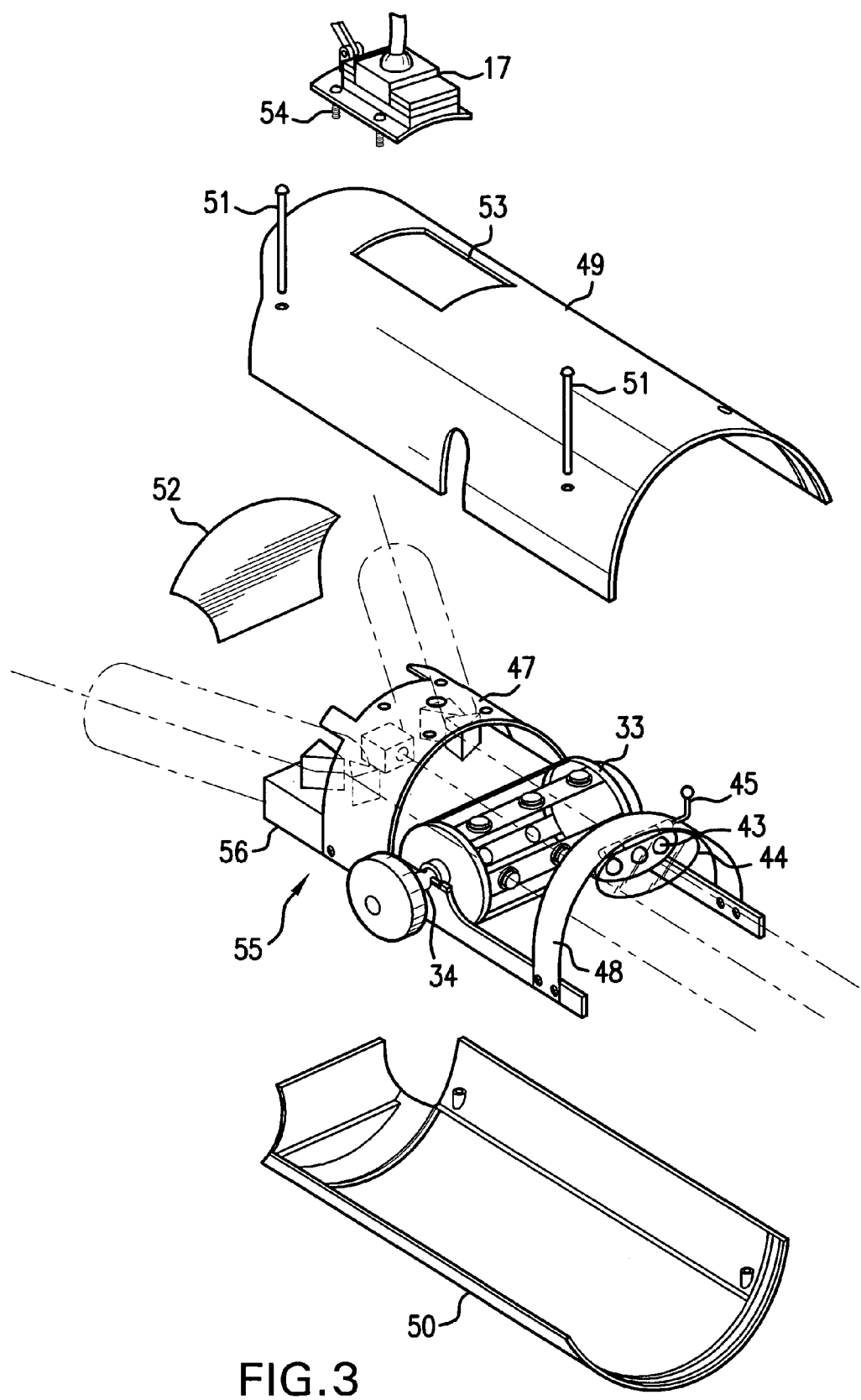
FIG. 3 is an exploded view of the stereo microscope.

Housing 26, as shown in FIG. 3, includes an internal mount 55 having a base section 56 on which the lens magnification changer 33, prism assemblies 31, oculars 27 and camera 38 are mounted. Rigid straps 47 and 48 are attached to the base section 56 by suitable means such as rivets or screws. Upper housing shell 49 and lower housing shell 50 are attached about internal mount 55 by screws 51 which are screwed into lower housing shell 50. Objective lens 32 is held in place in the housing 26 by one or more screw threaded members 51 which are screwed into an end of the housing 26. A plate 52 which is positioned in a groove in the upper housing shell 49 and mates with the lower housing shell helps to complete the housing 26.

Figure 4:
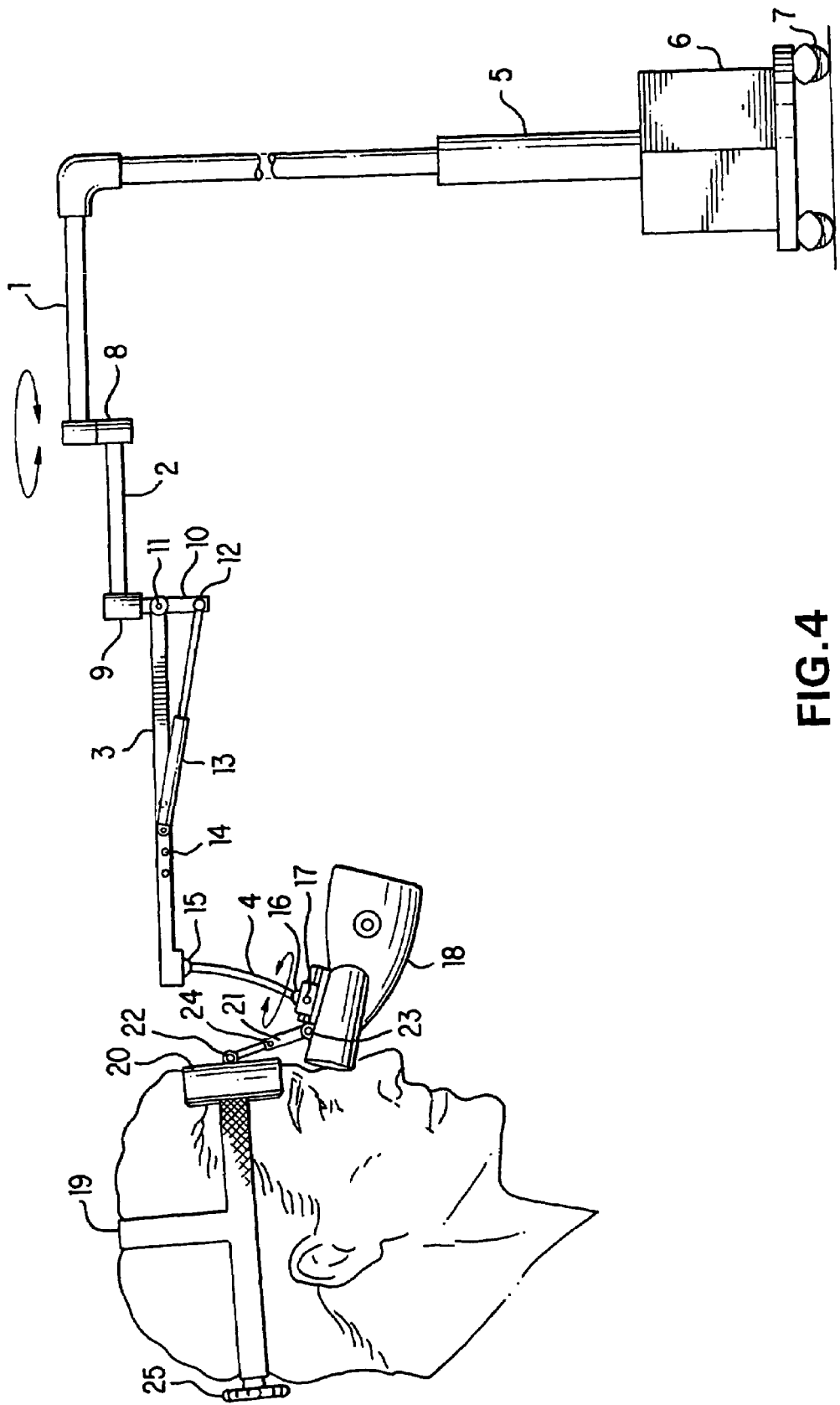
FIG. 4 is a support system for the microscope.

FIG. 4 shows an apparatus support and guidance system for the stereo microscope and is a separate subject of invention as disclosed in copending application Ser. No. 10/320,385 filed Dec. 17, 2002. A housing 6 on wheels 7 includes a telescoping device 5. The telescoping device may be raised or lowered by means of a rack and pinion, motorized screw or hydraulic piston and cylinder for example. The apparatus may also be supported by attaching an arm of the apparatus to a wall or ceiling mount or to an adjustable in length mount connected to a dental chair accessory pole.

A system of arms connects a microscope 18 to the telescoping portion 5. A first arm 1 is connected to the telescoping portion 5 at one end and to a second arm 2 at the other end by a bearing 8. The second arm 2 is connected to a third arm 3 by means of a bearing 9 including a vertical extension 10 at 11. A compressed gas spring 13 is pivotally connected at one end to the vertical extension 10 at 12 and at an opposite end to the third arm 3. The compressed gas spring 13 applies a counterbalancing force which is required for the setting of an equilibrium condition upon alteration of the third arm in a vertical direction. The third arm 3 has a plurality of perforations such as 14 wherein the attached location of the compressed gas spring 13 can be varied to adjust the force applied by the compressed gas spring against the arm 3. A forth arm 4 is attached to the third arm 3 at one end by a ball joint 15, allowing pivoting in any direction, and the opposite end to the microscope 18 by another ball joint 16. The ball joint 16 includes a combination cage and slide 17 attached to the microscope 18 as shown in FIG. 3. The cage and slide 17 extends through an opening 53 in the upper housing shell 49 and is attached to the rigid strap 47 by screws 54. The cage can move on the slide to help balance the microscope and can be held in place by a locking screw. Arm 2 can rotate 360 degrees at bearing 8, arm 3 can rotate 360 degrees at bearing 9 and arm 4 can rotate 360 degrees at both ball joints 15 and 16. The arm 4 can pivot at ball joints 15 and 16 in any direction.

An extension means 21 includes splined or noncircular in cross-section telescoping members which may be adjusted in length and locked in position by a setscrew 24. The extension means 21 is pivotally connected to both the microscope and to a head harness so that it can be adjusted relative to the head harness and microscope and held in position by lock screws 22 and 23. The head harness includes a padded member 20 and straps 19 attached about a clinician's head. The straps may be tightened by a belt-buckle arrangement, VELCRO members, a knob type tightener as shown at 25 or other conventional means.

What is claimed is:

1. A stereo microscope comprising: a hollow elongated body having opposite ends and enclosing first and second optical paths extending through the microscope, one of said ends having two oculars, each including an ocular lens assembly, a prism assembly in each optical path adjacent each ocular, a lens magnification changer rotatably mounted about an axis and located intermediate the ends of said hollow elongated body, a first series of bores located about the periphery of said lens magnification changer in a common plane and extending diametrically through said lens magnification changer, a second series of bores located about the periphery of said lens magnification changer in a common plane and extending diametrically through said lens magnification changer, a third series of bores located about the periphery of said lens magnification changer in a common plane and extending diametrically through said lens magnification changer, said second series of bores being axially located between said first and third series of bores of said lens magnification changer, said bores of said first and third series each including a lens assembly, the other of said ends of said hollow elongated body including an objective lens.

2. A stereo microscope as set forth in claim 1, further including a lens assembly located in at least one of said second series of bores.

3. A stereo microscope as set forth in claim 2, further comprising: a camera located in said hollow elongated body between said two oculars and said lens magnification changer and in line with one of said second series of bores.

4. A stereo microscope as set forth in claim 1, further comprising a camera located in said hollow elongated body between said two oculars and said lens magnification changer and in line with one of said second series of bores.

5. A stereo microscope as set forth in claim 4, wherein said first and second optical paths extend through said microscope and are located in a plane common to each path throughout said hollow elongated body.

6. A stereo microscope as set forth in claim 5, including means pivotally mounting said oculars in said plane that is common to said first and second optical paths.

7. A stereo microscope as set forth in claim 1, further comprising a light source located adjacent said objective lens in the other of said ends of said hollow elongated body.

8. A stereo microscope as set forth in claim 7, wherein said light source is either one or a group of LEDs.

9. A stereo microscope as set forth in claim 8, further comprising a wall, ceiling or vertical support mount, an adjustable arm attached at one end to said support mount and at an opposite end to said stereo microscope for supporting and positioning said stereo microscope, an attachment connecting said stereo microscope to the head of an operator.

10. A stereo microscope as set forth in claim 8, wherein said first and second optical paths extend through said microscope and are located in a plane common to each path throughout said hollow elongated body.

11. A stereo microscope as set forth in claim 10, including means pivotally mounting said oculars in said plane that is common to said first and second optical paths.

12. A stereo microscope as set forth in claim 1, wherein said two oculars, prism assemblies and lens magnification changer are mounted on a base section of an internal mount located within said hollow elongated body.

13. A stereo microscope as set forth in claim 12, wherein said hollow elongated body is formed by shells fastened together and enclosing said internal mount.

14. A microscope comprising: a hollow elongated body having opposite ends and enclosing first and second optical paths extending through said hollow elongated body, two oculars mounted at one of said ends, each ocular including a lens assembly, a prism assembly in each optical path adjacent each ocular, a lens magnification changer rotatably mounted about an axis and located intermediate the ends of said hollow elongated body, a first series of bores located about the periphery of said lens magnification changer in a common plane and extending diametrically through said lens magnification changer, a second series of bores located about the periphery of said lens magnification changer in a common plane and extending diametrically through said lens magnification changer, a lens assembly located in each bore of said first and second series, the other of said ends of said hollow elongated body including an objective lens, a first of said optical paths extending through one of said oculars to one of said prism assemblies, through one of said first series of bores of said lens magnification chamber and through said objective lens, a second of said optical paths extending through the other of said oculars to another of said prism assemblies, through one of said second series of bores in said lens magnification changer and through said objective lens, one or more light emitting diodes located in said hollow elongated body adjacent said objective lens.

15. A microscope as set forth in claim 14, further including a reflector behind said one or more light emitting diodes and a pivotally mounted light filter in front of said one or more light emitting diodes.

16. A microscope as set forth in claim 15, including a beam splitter located in one of said optical paths to allow one portion of light to pass from said objective lens to one of said oculars and to reflect another portion of light to a camera located exterior of said hollow elongated body.

17. A microscope as set forth in claim 14, including means pivotally mounting said oculars in a plane that is common to said first and second optical paths.

18. A microscope as set forth in claim 14, further including a wall, ceiling or vertical support mount, an adjustable arm attached at one end to said support mount and at an opposite end to said microscope by a connection allowing pivoting at the microscope in any direction and for supporting and positioning said microscope, an attachment connecting said microscope to the head of an operator for positioning of the microscope by the head of an operator.

19. A microscope as set forth in claim 14, including a beam splitter in one of said optical paths to allow one portion of light to pass from said objective lens to one of said oculars and to reflect another portion of light to a camera located exterior of said hollow elongated body.

20. A stereo microscope as set forth in claim 14, wherein said two oculars, prism assemblies and lens magnification changer are mounted on a base section of an internal mount located within said hollow elongated body.

21. A stereo microscope as set forth in claim 20, wherein said hollow elongated body is formed by shells fastened together and enclosing said internal mount.

22. A microscope as set forth in claim 14 wherein said first and second optical paths lie in a common plane.

23. A microscope comprising: a hollow elongated body having first and second ends and enclosing first and second optical paths extending through said hollow elongated body, an internal mount, located in said hollow elongated body, having a base section extending from a first of said ends toward a second of said ends, two oculars mounted on a first end of said base section and at a first end of said hollow elongated body, a prism assembly located on said base section adjacent each ocular, said base section having a second end opposite said first end, a lens magnification changer located on said base section intermediate said first and second ends, a first series of bores located about the periphery of said lens magnification changer in a common plane and extending diametrically through said lens magnification changer, a second series of bores located about the periphery of said lens magnification changer in a common plane and extending diametrically through said lens magnification changer, said hollow elongated body including an upper housing shell removably connected to said internal mount by fastening means and enclosing said lens magnification changer, prism assemblies and part of said oculars, an objective lens located at said second end of said hollow elongated body, one or more light emitting diodes located in said hollow elongated body and adjacent said objective lens.

24. The microscope of claim 23 wherein said hollow elongated body includes a lower housing shell located below said internal mount and connected to said internal mount and said upper housing shell.

25. The microscope of claim 24, wherein said oculars, prism assemblies, lens magnification changer and objective lens lie in a common plane.

26. The microscope of claim 25, wherein said oculars are mounted on said internal mount for movement relative to each other.

27. The microscope of claim 23, further including a reflector behind said one or more light emitting diodes and a pivotally mounted light filter in front of said one or more light emitting diodes.

28. The microscope of claim 23, including a wall, ceiling or vertical support mount, an adjustable arm attached at one end to said support mount and at an opposite end to said microscope by a joint allowing pivotal movement at said microscope in any direction and for supporting and positioning said microscope, an attachment for connecting said microscope to the head of an operator.

29. The microscope of claim 23, including a beam splitter located in an optical path extending through said objective lens and one of said bores of said lens magnification changer to allow one portion of light to pass from said objective lens to one of said oculars and to reflect another portion of light to a camera located exterior of said hollow elongated body.

* * * * *